US005429600A

United States Patent [19]

Heinke

[11] Patent Number: 5,429,600
[45] Date of Patent: Jul. 4, 1995

[54] METHOD FOR DELIVERING A PHARMACEUTICAL INTO THE NOSTRIL OF AN ANIMAL

[76] Inventor: Richard M. Heinke, 5120 NW. 38th St., Lincoln, Nebr. 68501

[21] Appl. No.: 236,275

[22] Filed: May 2, 1994

[51] Int. Cl.$^6$ ............................................. A61M 31/00
[52] U.S. Cl. ........................................ 604/54; 604/56; 604/87; 604/192
[58] Field of Search .................... 128/200.14, 207.18, 128/747; 604/49, 54, 56, 73, 77, 94, 187, 192, 198, 200–202, 218, 244, 82, 87, 226, 231

[56] References Cited

U.S. PATENT DOCUMENTS

| 2,512,568 | 6/1950 | Saffir | 604/239 |
| 3,506,006 | 4/1970 | Lange | 604/200 X |
| 3,874,381 | 4/1975 | Baum | 128/200.14 |
| 4,300,545 | 11/1981 | Goodnow et al. | 128/200.14 |
| 4,381,773 | 5/1983 | Goodnow et al. | 604/54 X |
| 5,242,418 | 9/1993 | Weinstein | 604/192 |
| 5,290,254 | 3/1994 | Vaillancourt | 604/192 |
| 5,295,972 | 3/1994 | Mischenko | 604/192 |

*Primary Examiner*—Corrine Maglione
*Attorney, Agent, or Firm*—Zarley, McKee, Thomte Voorhees & Sease; Dennis L. Thomte

[57] ABSTRACT

A syringe is described including a plastic barrel having a unitary needle extending from one end thereof which is normally shielded by a nasal tip-seal cap. A plunger is movably mounted in the barrel for aspirating the contents of the barrel or for drawing liquid into the barrel. The nasal tip-seal cap may be deflected or compressed with respect to the shielded needle so that the needle will pierce therethrough to enable the needle to be in communication with the interior of a pharmaceutical vial. The method of using the syringe of the invention to nasally vaccinate an animal or nasally vaccinate a human is also described.

4 Claims, 2 Drawing Sheets

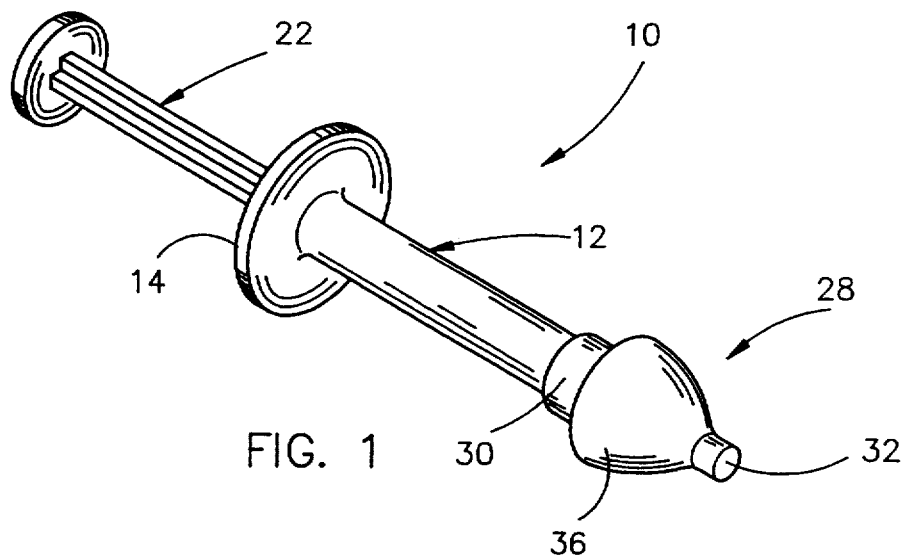
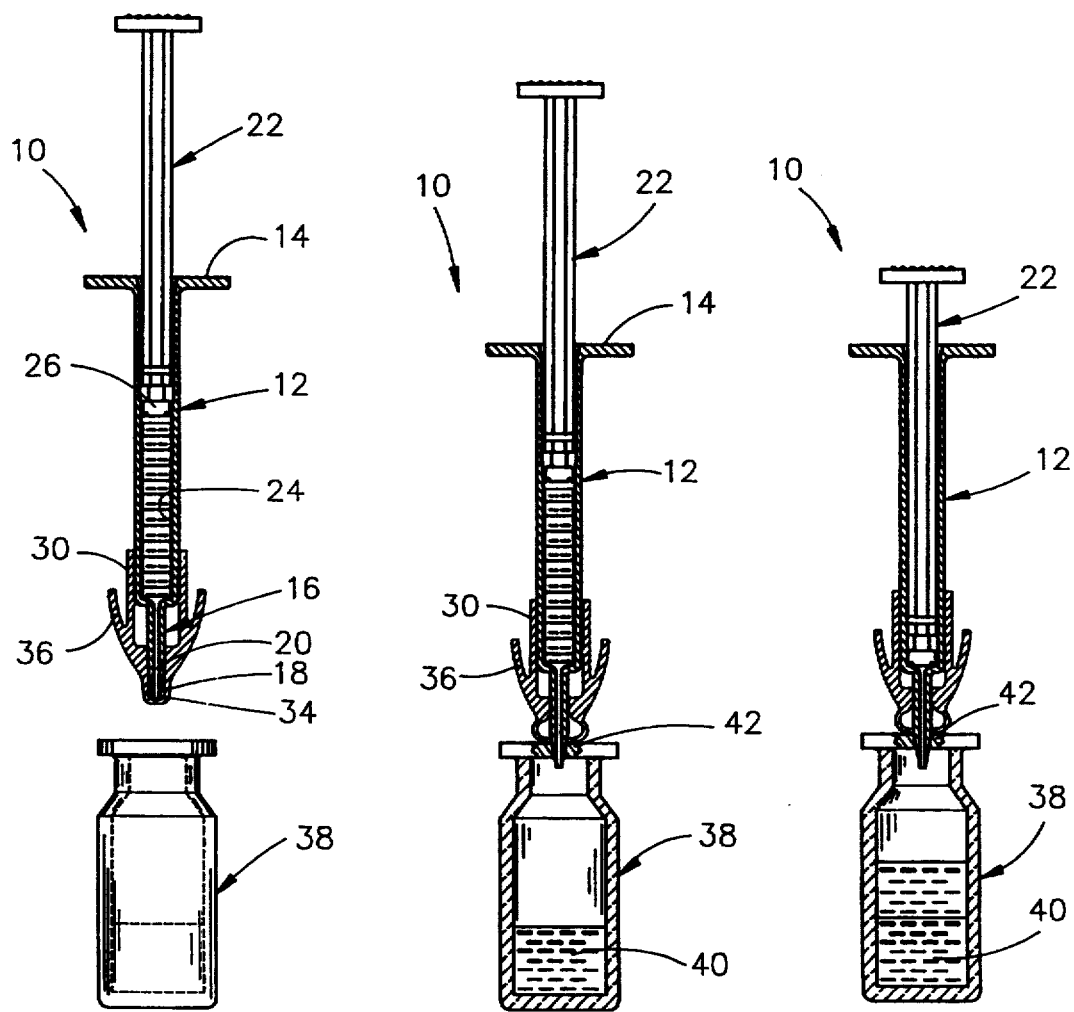
FIG. 1
FIG. 2  FIG. 3  FIG. 4

METHOD FOR DELIVERING A PHARMACEUTICAL INTO THE NOSTRIL OF AN ANIMAL

BACKGROUND OF THE INVENTION

1. Field of the Invention

This invention relates to a method and means for delivering a pharmaceutical, i.e., vaccine, into the nostril of an animal such as a cat, dog, etc., and more particularly to an improved syringe for use in vaccinating such an animal. The syringe could also be used to nasally aspirate a vaccine into the nostril of a human, if so desired.

2. Description of Related Art

Animals such as dogs and cats are frequently vaccinated by injecting the vaccine into one of the nostrils of the animal. For example, see U.S. Pat. No. 4,300,545 which discloses a method and nozzle for nasal vaccination of immature mammals.

A problem associated with the prior syringes and methods is the large number of steps which are necessary to prepare the syringe, vaccine, etc., for subsequent introduction into the nostril of the animal. Further, it is believed that the prior methods of preparing the syringe for use may result in an improper preparation of the vaccine and possible contamination thereof.

SUMMARY OF THE INVENTION

A syringe is disclosed which may be used to deliver a pharmaceutical such as a vaccine or the like into one of the nostrils of the animal. The syringe could also be used to inject a vaccine into a human, if so desired. The syringe comprises an elongated and hollow plastic barrel having a first compartment provided therein which extends inwardly into the rearward end thereof and which is adapted to receive a plunger therein. The barrel has a plastic needle at its forward end which has a pointed distal end. The barrel and the needle are of one-piece construction and are preferably comprised of a suitable injection molded plastic such as a polycarbonate material. A flexible nasal tip and seal cap is mounted on the forward end of the barrel which normally encloses the needle but which may be deflected with respect to the needle to permit the pointed distal end of the needle to pierce therethrough to expose the pointed distal end of the needle. The plunger may be moved inwardly into the barrel to aspirate the contents thereof outwardly through the needle. Conversely, the plunger may be moved outwardly with respect to the barrel to draw a liquid material thereinto.

The first compartment of the syringe is filled with a diluent such as sterile water or the like and the syringe may be enclosed within a sealed pouch at the factory, if so desired. When it is desired to vaccinate an animal, the syringe is first removed from its sealed pouch. A vial having a flexible cap thereon is provided which has the concentrated vaccine, preferably in a freeze-dried form and comprising a serum, therein. The syringe is positioned above the vial with the flexible nasal tip and the seal cap positioned against the rubber stopper cap of the vial. Downward force is then applied to the syringe to cause the pointed distal end of the plastic needle to pierce through the nasal tip and rubber stopper cap seal so that the needle penetrates through the rubber stopper cap seal of the vial and is in communication with the interior of the vial. The diluent is then injected into the vial. The syringe needle is then withdrawn from the vial. The vaccine and diluent is then mixed by shaking the vial. After the vaccine and diluent have been mixed, the needle is again introduced into the interior of the vial. The plunger is withdrawn with respect to the barrel so that the contents of the vial are drawn into the first compartment of the barrel. After the contents of the vial have been drawn into the first compartment of the barrel of the syringe, the syringe is removed from the vial which causes the nasal tip and cap seal to resume its normal shape to shield the pointed distal end of the needle. The nasal tip and cap seal is then introduced into the nostril of an animal and the plunger is moved forwardly or inwardly with respect to the barrel to aspirate the vaccine into the nasal passages of the animal.

It is therefore a principal object of the invention to provide an improved syringe for use in the vaccination of an animal or a human, if so desired.

A further object of the invention is to provide an improved method of vaccinating an animal which ensures that the vaccine will not be contaminated during the preparation of the syringe or the vaccine.

Yet another object of the invention is to provide a syringe which includes a nasal tip and cap seal on one thereof which normally shields a pointed needle but which may be deflected with respect to the needle so that the needle pierces the nasal tip and cap seal to enable the needle to penetrate the desired member.

These and other objects will be apparent to those skilled in the art.

BRIEF DESCRIPTION OF THE DRAWINGS

FIG. 1 is a front perspective view of the syringe of this invention;

FIG. 2 is a view illustrating the initial relationship of the syringe and the vial containing a serum;

FIG. 3 is a view similar to FIG. 2 except that the tip and cap seal of the syringe has been deflected to cause the needle to pierce through the tip and cap seal and through the rubber stopper cap on the vial;

FIG. 4 is a view similar to FIG. 3 except that the contents of the syringe have been injected into the vial;

DESCRIPTION OF THE PREFERRED EMBODIMENT

Figure 8:
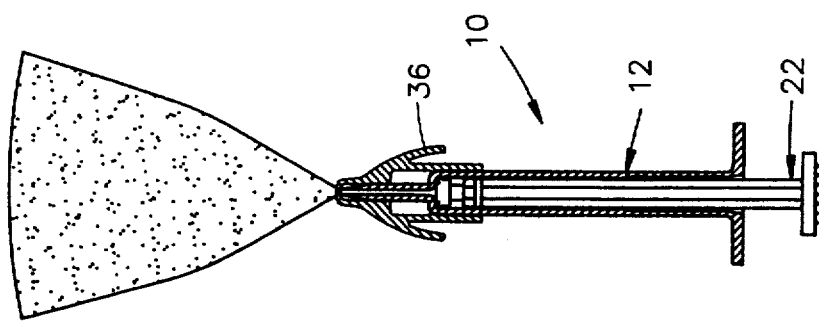
FIG. 8 is a view similar to FIG. 7 except that the plunger has been moved inwardly with respect to the barrel to aspirate the serum from the syringe.

The syringe of this invention is referred to generally by the reference numeral 10 and the same would preferably be enclosed in a sealed sterile pouch at the factory. Syringe 10 includes a barrel 12 having a rear opening stop 14 at one end and a needle 16 at its other end.

Preferably, barrel 12 and needle 16 are of one-piece construction and are preferably comprised of a suitable injection molded plastic such as a polycarbonate material. Needle 16 is provided with a pointed distal end 18. As seen in FIG. 2, needle 16 includes an elongated bore 20 extending therethrough.

Syringe 10 also includes piston-plunger assembly 22 which is adapted to be at least partially received in the rear opening of the barrel 12. Preferably, assembly 22 is comprised of a linear low density polyethylene material. For purposes of description, barrel 12 will be described as defining a first compartment 24. Piston-plunger assembly 22 includes a piston 26 which is adapted to sealably engage the inner walls of the first compartment 24 of the barrel 12 in conventional fashion. Compartment 24 of syringe 12 is filled with a suitable diluent such as sterile water or the like at the factory prior to the piston-plunger assembly 22 being positioned on the barrel 12. After the diluent is positioned in the compartment 24, the syringe 12 is enclosed within a suitable and conventional sealed pouch (not shown).

The numeral 28 refers to a nasal tip-cap seal which is mounted on the end of barrel 12 to shield the needle 16 and to prevent the leakage of the diluent from the syringe 10. Preferably, nasal tip-cap seal 28 is comprised of an injection molded elastomeric plastic material. Nasal tip-cap seal 28 includes a cylindrical portion 30 which is adapted to frictionally and sealably embrace the end of barrel 12. Nasal tip-cap seal 28 also includes a tip 32 which is positioned at the end of an internal cavity 34 which normally receives the distal end 18 of needle 16. Nasal tip-cap seal 28 further includes a skirt portion 36 which is adapted to provide a tapered shut-off type seal of the nostril opening of the animal to facilitate the delivery of the vaccine into one of the nostrils of the animal.

When it is desired to vaccinate an animal, the syringe 10 is first removed from its sealed pouch. The syringe 10 is then positioned with respect to the vial 38 as illustrated in FIG. 2. Syringe 10 is then moved downwardly with respect to the vial as illustrated in FIG. 3 so that the tip 32 contacts the rubber stopper cap 42 and so that the tip 32 is deflected or compressed to enable the pointed end 18 of the needle 16 to pierce the rubber stopper cap 42 so that the needle 16 is in communication with the interior of the vial 38 as illustrated in FIG. 3. Piston-plunger assembly 22 is then moved inwardly with respect to barrel 12 as illustrated in FIG. 4 to inject the diluent in the compartment 24 into the interior of the vial 38 as illustrated in FIG. 4. Once the diluent has been injected into the vial 38, the syringe 10 will normally be removed from the vial 38 to facilitate the mixing of the vaccine 40 and the diluent. However, the syringe 10 could remain in contact with the vial 38 during the mixing process if desired.

Figure 7:
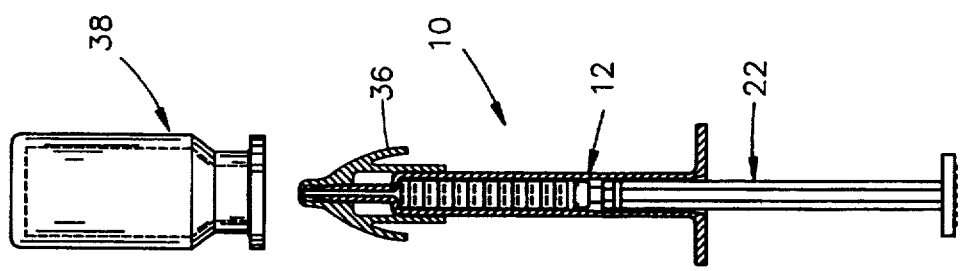
FIG. 7 is a view similar to FIG. 6 except that the syringe has been removed from the vial with the tip and cap seal again enclosing the needle.
Figure 6:
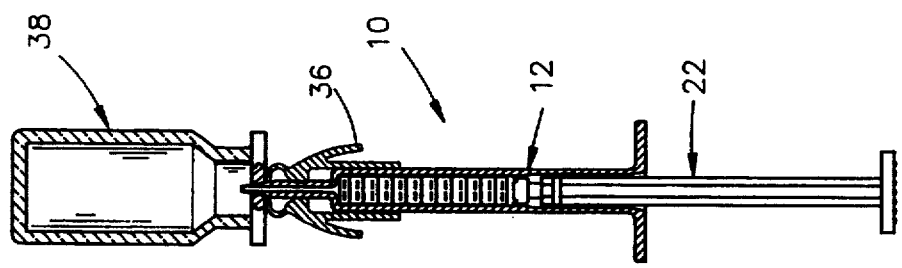
FIGS. 5 and 6 illustrate the manner in which the vaccine is withdrawn from the vial after it has been mixed.
Figure 5:
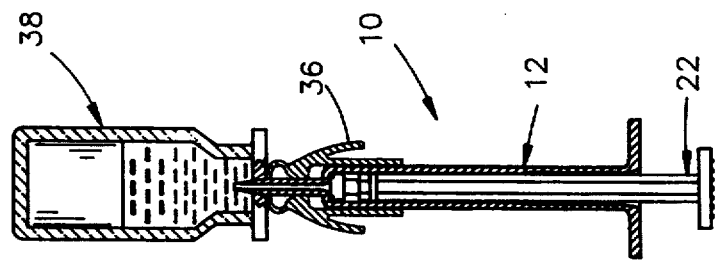

The vial 38 is then shaken until the diluent is completely mixed with the concentrated vaccine. If the syringe 10 has been removed from the vial 38 during the mixing operation, the syringe 10 is again positioned on the vial as illustrated in FIG. 5 so that the needle 16 is in communication with the interior of the vial. The syringe 10 and vial 38 are inverted as illustrated in FIG. 5. The piston-plunger assembly 22 is then withdrawn from the barrel 12 to cause the mixture in the vial 38 to be drawn into the interior of the barrel 12 as illustrated in FIG. 6. The syringe 10 is then removed from the vial 38 as illustrated in FIG. 7. The nasal tip-cap seal 28 is then inserted into the nostril of an animal. The piston-plunger assembly 22 is then moved forwardly or inwardly with respect to the barrel to aspirate the vaccine outwardly through the tip 32 of the nasal tip-cap seal 28. The vaccine is aspirated through the opening created in the tip 32 when the needle 16 pierced therethrough during the step illustrated in FIG. 3. The vaccine is aspirated through the orifice from the syringe 10 while the needle 16 is shielded within the nasal tip-cap seal 28 to prevent the animal from being stuck by the needle.

It can therefore be seen that a novel syringe has been provided which may be used to vaccinate an animal. It can also be seen that a novel method has been described for vaccinating animals which substantially reduces the steps normally associated with such a vaccination procedure and which ensures that the vaccine will not become contaminated during the mixing or delivery steps.

Although the invention is ideally suited for use in vaccinating an animal such as a cat, dog, etc., the syringe could also be used to vaccinate humans, if so desired by the same nasal method. The tip 32 acts as a shield to prevent inadvertent needle sticks when in its normal non-compressed position.

It can therefore be seen that the invention accomplishes at least all of its stated objectives.

I claim:

1. The method of delivering a pharmaceutical into the nasal passage of a living creature, comprising the steps of:

(a) providing a syringe including an elongated hollow barrel having a rearward end and a forward end and being comprised of a plastic material; said barrel having a rear opening at its rear end; said barrel having a rear opening stop provided thereon; said barrel having a first compartment provided therein which extends forwardly from said rear opening for receiving a plunger therein; said barrel having a hollow needle at its forward end, said needle having a proximal end in communication with said forward end of said barrel and a pointed distal end; a flexible tip and cap seal mounted on the forward end of said barrel which normally encloses said needle but which may be deflected rearwardly with respect to said needle to permit said pointed distal end of said needle to pierce therethrough to expose said pointed distal end of said needle; and a plunger selectively movably mounted on said first compartment of said barrel including a piston mounted thereon for aspirating any material in said first compartment through said needle when said plunger is moved forwardly into said first compartment and for drawing material inwardly through said needle and into said first compartment when said plunger is moved rearwardly with respect to said barrel;

(b) providing a vial which has a freeze-dried pharmaceutical therein and which is maintained therein by a cap means;

(c) placing a diluent in said first compartment;

(d) positioning said flexible tip and seal cap on said cap means;

(e) longitudinally moving said barrel of said syringe with respect to said vial to cause said needle to pierce through said tip and cap seal and to pierce through said cap means of said vial so that said pointed distal end of said needle is in communication with the interior of said vial;

(f) moving said plunger with respect to said barrel to aspirate the diluent in said compartment into said vial;

(g) mixing the diluent with the pharmaceutical;

(h) moving said plunger with respect to said barrel to draw the pharmaceutical-diluent mixture from said vial into said first compartment;

(i) disengaging said syringe from said vial so that said needle is again enclosed by said tip and cap seal;

(j) inserting the tip and cap seal into the nostril of the living creature;

(k) moving said plunger inwardly into said barrel to aspirate the pharmaceutical-diluent mixture into the nostril of the living creature; and (l) removing the tip and cap seal from the nostril of the living creature.

2. The method of claim 1 wherein said diluent is sterile water.

3. The method of claim 1 wherein said freeze-dried pharmaceutical comprises a serum.

4. The method of claim 1 wherein said pharmaceutical-diluent mixture comprises a vaccine.

* * * * *